United States Patent [19]
Van Waeg et al.

[11] Patent Number: 5,676,645
[45] Date of Patent: Oct. 14, 1997

[54] METHOD AND APPARATUS FOR CONTROLLING CONCENTRATIONS IN VIVOS AND IN TUBING SYSTEMS

[75] Inventors: Geert Van Waeg, Brussel, Belgium; Robert W. Langley, Westminster; Larry Joe Dumont, Arvada, both of Colo.

[73] Assignee: COBE Laboratories, Inc., Lakewood, Colo.

[21] Appl. No.: 472,931

[22] Filed: Jun. 6, 1995

Related U.S. Application Data

[63] Continuation-in-part of Ser. No. 845,677, Mar. 4, 1992, Pat. No. 5,421,812.

[51] Int. Cl.$^6$ .................................................. A61M 1/00
[52] U.S. Cl. ........................... 604/4; 604/65; 604/67
[58] Field of Search ......................... 604/4, 5, 6, 65, 604/67, 19, 27, 403, 407

[56] References Cited

U.S. PATENT DOCUMENTS

| | | | |
|---|---|---|---|
| 3,916,892 | 11/1975 | Latham, Jr. | 128/214 |
| 4,000,972 | 1/1977 | Braun et al. | 23/230 |
| 4,447,191 | 5/1984 | Bilstad et al. | 417/12 |
| 4,458,539 | 7/1984 | Bilstad et al. | 73/861 |
| 4,481,827 | 11/1984 | Bilstad et al. | 73/861 |
| 4,501,531 | 2/1985 | Bilstad et al. | 417/63 |
| 4,540,406 | 9/1985 | Miles | 604/269 |
| 4,573,961 | 3/1986 | King | 604/6 |
| 4,592,743 | 6/1986 | Hjertman et al. | 604/82 |
| 4,598,733 | 7/1986 | Kanno et al. | 137/406 |
| 4,648,866 | 3/1987 | Malbrancq et al. | 604/5 |
| 4,655,742 | 4/1987 | Vantard | 604/6 |
| 4,657,529 | 4/1987 | Prince et al. | 604/6 |
| 4,708,714 | 11/1987 | Larsson et al. | 604/5 |
| 4,736,748 | 4/1988 | Nakamura et al. | 128/632 |
| 4,769,001 | 9/1988 | Prince | 604/4 |
| 4,795,314 | 1/1989 | Prybella et al. | 417/43 |
| 4,850,995 | 7/1989 | Tie et al. | 604/6 |
| 4,850,998 | 7/1989 | Schoendorfer | 604/28 |
| 4,923,598 | 5/1990 | Schäl | 210/87 |
| 4,968,295 | 11/1990 | Neumann | 604/6 |
| 4,995,268 | 2/1991 | Ash et al. | 604/4 X |
| 5,092,836 | 3/1992 | Polaschegg | 604/4 |
| 5,112,298 | 5/1992 | Prince et al. | 604/6 |
| 5,378,227 | 1/1995 | O'Riordan et al. | 604/4 |
| 5,421,812 | 6/1995 | Langley et al. | 604/4 |

Primary Examiner—Sam Rimell
Assistant Examiner—Robert V. Racunas
Attorney, Agent, or Firm—Bruce R. Winsor; Edna M. O'Connor

[57] ABSTRACT

A method and apparatus for maximizing the total amount of blood processed during an apheresis procedure by optimizing the concentration of anticoagulant in a donor/patient and the associated extracorporeal tubing set is provided. A simplified model of an anticoagulant accumulation in a donor/patient's body is used to calculate an optimal anticoagulant infusion rate profile to the donor/patient during a blood processing procedure. A maximum acceptable anticoagulant concentration in the donor/patient acts as an upper limit on the rate at which anticoagulant may be infused to the donor/patient using the optimized infusion rate profile. A minimum acceptable anticoagulant level acts as a lower limit in optimally controlling the anticoagulant concentration in the extracorporeal tubing set. Both the maximum acceptable anticoagulant level in the donor/patient and the minimum acceptable anticoagulant level in the extracorporeal tubing set may be customized for a specific donor/patient thereby allowing the optimized infusion rate profile and the extracorporeal tubing set anticoagulant concentration to be customized for the specific patient.

15 Claims, 3 Drawing Sheets

METHOD AND APPARATUS FOR CONTROLLING CONCENTRATIONS IN VIVOS AND IN TUBING SYSTEMS

CROSS REFERENCE PATENTS

This application is a continuation-in-part of application Ser. No. 07/845,677, filed Mar. 4, 1992, now U.S. Pat. No. 5,421,812, of which the entire disclosure is incorporated herein by reference.

FIELD OF INVENTION

The present invention relates to the field of fluid tubing systems, and in particular, to controlling the flow rate and concentration of one or more constituents in an extracorporeal tubing system and in a patient or donor. More particularly, the present invention relates to controlling the flow rate and concentration of a constituent, such as an anticoagulant, in a blood tubing set used for blood processing, such as apheresis procedures, and in the donor/patient to which the tubing system is connected.

BACKGROUND OF THE INVENTION

The efficiency of apheresis procedures depends largely on the amount of blood processed during a given procedure time. The amount of blood processed is directly related to the inlet flow rate of blood from a patient (in the case of a person whose blood is being treated) or donor (in the case of a person donating a blood component) into an extracorporeal tubing set of a blood processor. The term "donor" used in the claims will refer to either a patient or a donor or both. Reference to a "generic" donor/patient refers to a hypothetical average donor/patient in a class of donors exhibiting statistically determined "normal" physiological characteristics for that class.

The greater the inlet flow rate of a donor/patient's whole blood into the extracorporeal tubing set, during a given procedure time, the greater the amount of blood processed during the procedure. There are, however, limitations on the inlet flow rate. For example, anticoagulants are required during apheresis procedures to prevent hemostasis and to permit blood processing. Anticoagulants are typically added to the extracorporeal tubing set and are, therefore, also infused to the donor/patient. Generally, the higher the flow rate at which an anticoagulant is added to an extracorporeal tubing set, the higher a donor/patient's inlet flow rate may be and, therefore, the greater the amount of blood that may be processed during the given procedure time. Furthermore, it is important that the concentration of anticoagulant in the extracorporeal tubing set be maintained at a sufficiently high level. If there is not sufficient anticoagulant in the extracorporeal tubing set, clumping and platelet activation or both may occur.

It is very important, however, that the rate at which the anticoagulant is returned or infused back to a donor/patient during blood processing procedures is not too rapid. Infusing anticoagulant to a donor/patient more rapidly than it can be removed by the donor/patient's metabolic, renal or other clearance processes will result in an increase in the concentration of anticoagulant in the donor/patient. If the concentration of anticoagulant in the donor/patient becomes too high, adverse physiological reactions may occur. This limit on the concentration of anticoagulant that a donor/patient may tolerate also limits the inlet flow rate and, therefore, the amount of blood that may be processed.

Heparin and citrate containing solutions, such as acid citrate dextrose ("ACD"), are anticoagulants commonly used in various apheresis procedures. Citrate prevents blood coagulation by binding ionized calcium which is required for coagulation. Ionized calcium, however, is also important for a variety of other physiological functions such as skeletal and cardiac muscle contraction and nerve function. Hypocalcemia, a decrease in ionized calcium, is associated with tetany and cardiac failure. Anxiety, chills, convulsions, among others, are further side effects that can occur when citrate is infused too rapidly into a donor/patient.

Heparin interferes with coagulation by preventing the formation of thrombin from prothrombin. Too much heparin may result in hypotension and flushing. Furthermore, heparin typically has a long half life resulting in heparin anticoagulating a donor/patient's blood for long time periods following the blood processing procedure. It is, therefore, desirable to carefully control the amount of anticoagulant maintained in the blood processor's extracorporeal tubing set and the amount infused into a donor/patient while simultaneously maximizing the amount of blood processed.

In the past, anticoagulant levels in extracorporeal tubing systems and in donor/patients have been controlled indirectly and imprecisely by controlling the delivery rate at which anticoagulant is added to the extracorporeal tubing set of a blood processing unit without any direct control of the rate of infusion of the anticoagulant into the donor/patient. Such an approach is inexact because it does not account for the anticoagulant removed from the extracorporeal tubing set by the procedure itself before the anticoagulated blood is returned to the donor/patient. For example, a significant volume of anticoagulant is drawn off in the plasma collect line during plasma collection procedures and in the cell collect line during cell harvesting procedures. Additionally, the described approach does not account for unmetabolized anticoagulant added to the tubing set from the donor/patient due to recirculation, nor does it account for anticoagulant added to the tubing set by replacement fluids, such as plasma or albumin during total plasma exchange procedures. Furthermore, the described approach delivers anticoagulant to the tubing set at a constant rate for the duration of the procedure. The described approach, therefore, also infuses anticoagulant to the donor/patient at a substantially constant anticoagulant infusion rate for the duration of the procedure.

Some approaches account for anticoagulant removed from the extracorporeal tubing set in determining the amount of anticoagulant being infused to the patient. Even these more current approaches, however, infuse anticoagulant to the patient at a constant rate throughout the procedure. Current approaches, therefore, do not maximize the amount of blood that may be processed during a given procedure because they do not account for the molecular interactions in a donor/patient's blood with the infused anticoagulant. For example, current approaches do not account for the dynamics of donor/patient renal excretion, renal reabsorption, or metabolic clearance of the infused anticoagulant, when setting the infusion rate at which anticoagulant is infused to a donor/patient. Rather, current approaches infuse anticoagulant to a donor/patient at a constant rate for the duration of the procedure.

At present, this constant infusion rate of anticoagulant to the donor/patient is often empirically derived for all potential patients/donors. Typically, the constant infusion rate is set at a level that has been observed to result in few physiological side effects for most donors/patients. If side effects are observed with this infusion rate, a medical care worker typically reduces the infusion rate downward. Some approaches do account for variations between patients/donors in a very general way. For example, some approaches consider a donor/patient's total blood volume as a rough surrogate for the metabolic capacity of the donor/patient in setting the constant anticoagulant infusion rate. This generally applicable infusion rate is problematic because the concentration of anticoagulant that a donor/patient may tolerate varies from donor/patient to donor/patient; therefore, an infusion rate profile that would be tolerated in one donor/patient, would cause side effects in another donor/patient or could be increased, to process more blood, in still another donor/patient.

Some current approaches, that account for anticoagulant removed from the tubing set in determining anticoagulant levels in the tubing set, do vary anticoagulant concentrations in the extracorporeal tubing set, during the apheresis procedure, in a rough step by step fashion in response to the observation that more anticoagulant is required towards the beginning of a procedure than towards the end of a procedure to prevent clumping and/or clotting. Furthermore, the described approaches do not account for recirculated unmetabolized anticoagulant when varying the extracorporeal anticoagulant levels. The described stepwise variation often results in sudden changes in fluid flow rates, such as inlet flow rates. Unnecessary abrupt changes in fluid flow rates may be less desirable than a gradual change. This may decrease the quality and/or purity of collected blood components, such as platelets in a plateletpheresis procedure.

This step wise variation is empirically derived to be generally applicable to most patients/donors. Because it is derived for a generic donor/patient, this still may be problematic because the concentration of anticoagulant required in the extracorporeal tubing set to prevent clumping and/or clotting also varies from donor/patient to donor/patient. Using a generally applicable variable extracorporeal anticoagulant level may result in maintaining a higher than necessary anticoagulant concentration in the tubing set.

It is, therefore, desirable to optimize the control of the rate of anticoagulant infusion to a donor/patient to increase the amount of blood that may be processed in a given procedure without adverse physiological side effects, and to optimize the control of the concentration of anticoagulant maintained in an associated extracorporeal tubing set to minimize clumping and/or clotting. It is also desirable to control these anticoagulant levels specifically for a given donor/patient rather than generally for a broad class of donors/patients.

U.S. patent application Ser. No. 07/845,677, filed Mar. 4, 1992, now U.S. Pat. No. 5,421,812, and incorporated herein in its entirety by reference, describes significant advances in the control of anticoagulant during an apheresis procedure. It is against this background that the further significant advances of the present invention developed.

SUMMARY OF THE INVENTION

A significant aspect of the present invention is a method and apparatus for maximizing the volume of blood processed during an apheresis procedure while minimizing the probability of adverse donor/patient reactions.

Another significant aspect of the present invention is a method and apparatus for maximizing the volume of blood processed during an apheresis procedure while minimizing the level of anticoagulant in a blood processor's extracorporeal tubing set.

Another significant aspect of the present invention is a method and apparatus for increasing the inlet flow rate of anticoagulated blood, thereby either increasing the amount of blood processed during a given procedure time, or decreasing the procedure time.

Another significant aspect of the present invention is method and apparatus for increasing the inlet flow rate by varying the anticoagulant infusion rate to a patient as a function of time to account for anticoagulant accumulation in the patient including physiological processing of the infused anticoagulant.

Another significant aspect of the present invention is a method and apparatus for varying the anticoagulant delivery rate to an extracorporeal tubing set as a function of time to account for unmetabolized anticoagulant recirculated to the extracorporeal tubing set.

Another significant aspect of the present invention is a method and apparatus for optimizing the inlet flow rate by infusing anticoagulant to a patient at an infusion rate profile that will allow faster anticoagulant accumulation in the donor/patient without exceeding a maximum acceptable patient anticoagulant level during the procedure.

Another significant aspect of the present invention is a method and apparatus for gradually varying anticoagulant concentrations in the extracorporeal tubing set at a rate that will maintain the tubing set's anticoagulant level above a time dependent minimum acceptable level throughout the procedure, thereby preventing clumping and platelet activation in the extracorporeal blood.

Another significant aspect of the present invention is a method and apparatus for determining a maximum acceptable anticoagulant level for a specific patient.

Another significant aspect of the present invention is a method and apparatus for determining a minimum acceptable anticoagulant level in an extracorporeal tubing set for a specific patient.

In accordance with these aspects, the present invention includes a method and apparatus for increasing the inlet flow rate of anticoagulated donor/patient blood in a blood processor's extracorporeal tubing set by optimizing the anticoagulant infusion rate to the patient. The present invention includes a blood processor having an extracorporeal tubing set. The tubing set may include, an inlet line for receiving whole blood from a patient, an anticoagulant line for adding anticoagulant to the inlet line whole blood, various collect lines for harvesting fractionated blood components, a replacement line for adding a fluid to the system, and an outlet line for returning anticoagulated uncollected blood or blood components to the donor/patient. Peristaltic pumps are associated with some or all of these lines to move fluid through the respective lines at controlled flow rates. A controller regulates the speed of each pump and, therefore, the flow rate of each fluid through the associated tubing line. The anticoagulant concentration in the inlet line may be varied independently from the anticoagulant concentration in the outlet line.

A donor/patient can only tolerate a given level of anticoagulant. Once that level is exceeded, the donor/patient will experience adverse physiological side effects. This maximum acceptable anticoagulant level is donor/patient specific, meaning the level of citrate that will trigger adverse side effects varies from donor/patient to donor/patient. This maximum acceptable anticoagulant level limits the rate and amount of anticoagulant that may be infused into a donor/patient which limits the delivery rate of anticoagulant to a tubing set which also limits the inlet flow rate which, finally, limits the amount of blood processed during a given procedure.

The present invention models the rate at which citrate accumulates in a generic donor/patient's body as a function of time. In modeling this accumulation, the present invention accounts for several physiological factors including renal citrate excretion, renal citrate reabsorption, metabolic citrate clearance and endogenous citrate production. The present invention uses this modeled anticoagulant accumulation to calculate an optimal infusion rate profile that will increase the amount of blood processed during the procedure by allowing faster accumulation of the anticoagulant in a generic donor/patient without exceeding a maximum acceptable anticoagulant level determined for the generic donor/patient. By optimizing the infusion rate in this manner, the present invention increases the inlet flow rate mainly at the beginning of a procedure, thereby, increasing the total amount of blood that may be processed during a given procedure.

The present invention, also using the above model, predicts the amount of unmetabolized anticoagulant or citrate, that will be recirculated from the donor/patient to the extracorporeal tubing set as a function of time. The present invention adjusts the ratio of inlet flow rate to anticoagulant flow rate ("inlet/AC ratio") with time to account for the increasing citrate concentration in donor/patient blood recirculated to the inlet line. The present invention also adjusts the inlet/AC ratio with time to account for the higher level of extracorporeal anticoagulant observed to be needed towards the beginning of a procedure. This adjustment is done gradually without sudden changes in inlet flow rates or other flow rates in the extracorporeal tubing set.

Additionally, the present invention regulates the adjustment of the inlet flow rate to anticoagulant flow rate to vary with time while maintaining the extracorporeal anticoagulant level above a predetermined minimum acceptable anticoagulant level. The term "level" shall herein refer to concentration or total quantity. This predetermined minimum acceptable anticoagulant level also varies with time and is preset at a level that prevents clumping and/or platelet activation. It has been observed that the minimum acceptable anticoagulant level required to prevent clumping and/or clotting is higher at a beginning of a procedure than at an end of the procedure. Once again this predetermined minimum acceptable level is donor/patient specific, meaning that the minimum level of anticoagulant required in an extracorporeal tubing set to prevent clumping and/or clotting varies from donor/patient to donor/patient.

The present invention allows both the maximum acceptable donor/patient anticoagulant level and the minimum acceptable anticoagulant level in the tubing set to be customized for a specific donor/patient. The present invention allows a prior donor/patient acceptable level to be stored in the memory of the controller for a specific donor/patient. If adverse effects are observed at the prior donor/patient acceptable level, the present invention may calculate a reduced donor/patient level for a specific patient and the new donor/patient acceptable level may be stored for the specific patient. Conversely, if no adverse effects are observed, the present invention may calculate an increased donor/patient acceptable level and the new higher donor/patient acceptable level may be stored. Similarly, donor/patient specific minimum acceptable anticoagulant levels required in the extracorporeal tubing set may be stored or recalculated and stored for a specific donor as they are ascertained.

Other aspects of this invention will appear from the following description and appended claims, reference being had to the accompanying drawings forming a part of this specification wherein like reference characters designate corresponding parts in the several views.

DETAILED DESCRIPTION OF THE PREFERRED EMBODIMENTS

Figure 1:
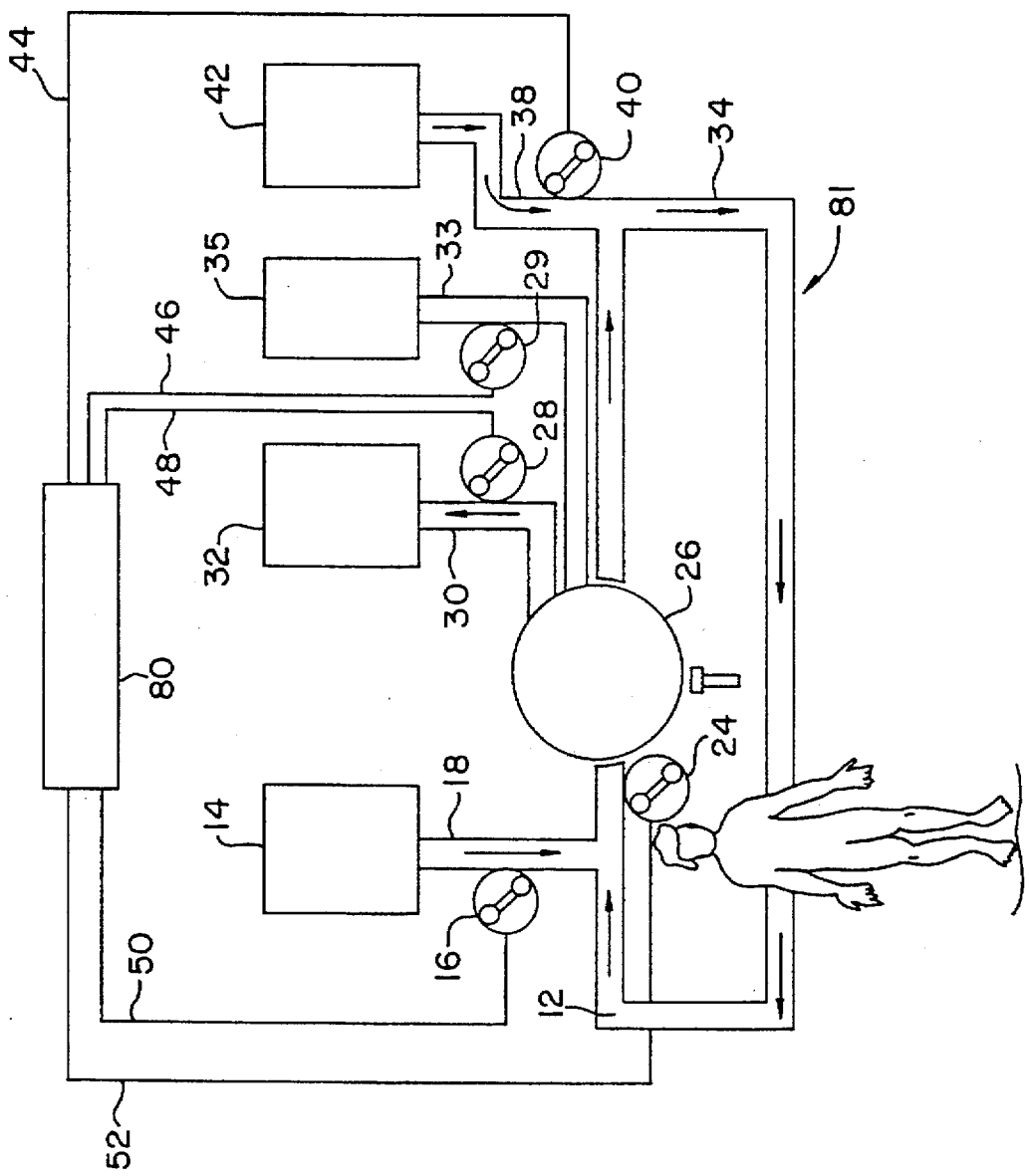
FIG. 1 shows the flow path for a hypothetical apheresis procedure where the invention is applicable.

The flow paths for a hypothetical blood apheresis procedure are shown in FIG. 1. The flow paths in FIG. 1 are not intended to depict any actual apheresis procedure, but instead are intended to be exemplary of the possible flow paths used for a variety of possible procedures. As explained below, actual procedures will generally not include all the flow paths shown in FIG. 1, but rather a subset of the depicted flow paths and may include additional flow paths (not shown). The subset of flow paths used for an actual procedure will depend the nature of that procedure. Further, FIG. 1 illustrates a dual needle procedure. It will be recognized by those skilled in the art that the present invention may be used with a single needle procedure as well.

The present invention will be described with respect to a citrate containing anticoagulant solution, in the text referred to as ACD. It will be understood by those skilled in the art, that the invention can be directly implemented with all citrate containing anticoagulant solutions, and acetate containing variants of them. It will also be understood by those skilled in the art, that the invention can be used with heparin, or any anticoagulant having a known decay rate in the body or decay profile that can be described by a biodynamic model, although some adjustment of variables may be required.

Whole blood is removed from a donor/patient into and through an inlet line 12. An anticoagulant, such as ACD, is pumped from an anticoagulant reservoir 14 by an anticoagulant pump 16 through an anticoagulant line 18 into the inlet line 12 of an extracorporeal tubing set 81. The whole blood with added anticoagulant is pumped by an inlet pump 24 to a separator system 26 at an inlet flow rate. The level of extracorporeal anticoagulant in the tubing set 81 may be expressed as a ratio of the inlet flow rate to the anticoagulant flow rate referred to in the text as inlet/AC ratio. The separator system 26 may be a centrifuge of the continuous flow type, such as the centrifuge used with the SPECTRA® brand apheresis system manufactured by COBE BCT, Inc. The separator system 26 may also be any other system of separating blood into its components such as other types of continuous and batch centrifuge systems and membrane separations systems. The present invention may also be adaptable to other extracorporeal circulation systems such as dialysis systems.

The separator system 26 may fraction the whole blood into a variety of blood components such as plasma, platelets, white blood cells, red blood cells or any combination of them. The plasma may be drawn off by a plasma pump 28 to a plasma collect line 30 and into a plasma collect bag 32. Cells may be drawn off by a cell pump 29 to a cell collect bag 35. A return line 34 returns to the donor/patient any components that are not collected. In fluid communication with the return line 34 is a replacement line 38. A replacement fluid pump 40 pumps replacement fluid from a replacement fluid reservoir 42 into the replacement fluid line 38. The outlet end of the return line 34 enters the donor/patient.

The flow through the various pumps may be monitored and controlled using a microprocessor based controller 80 connected to the various peristaltic pumps by conventional electrical interconnects 44, 46, 48, 50, and 52.

The inlet flow rate of whole blood and anticoagulant in the inlet line 12, determines how rapidly whole blood is removed from the donor/patient and, therefore, how much blood is processed during a given procedure time or, alternatively, how quickly the procedure may be carried out. The inlet flow rate is constrained by several practical considerations, including the maximum level of anticoagulant or citrate a donor/patient may tolerate without suffering adverse physiological side effects and the minimum level of anticoagulant that must be maintained in an extracorporeal tubing set to prevent clumping and/or clotting. It is impractical to measure the actual level of citrate that a donor/patient may tolerate without adverse side effects and that will prevent clumping and/or clotting in a tubing set for every donor/patient for every procedure. The present invention, therefore, estimates these values.

The maximum allowable donor/patient estimated citrate concentration ("MADEC") may be specified for a broad class of donors/patients in the present invention. The present invention may rely on published data and observation to empirically determine the MADEC below which a majority of patients/donors of a given class do not suffer adverse side effects. The present invention may also be adjusted to account for a MADEC that varies with time. Additionally, the present invention can determine the MADEC for a specific donor/patient as will be discussed in more detail below.

The anticoagulant level in a donor/patient may be varied independently of the anticoagulant level in the extracorporeal tubing set 81. The present invention may therefore determine a minimum estimated steady-state extracorporeal citrate concentration ("MESEC") in the tubing set 81 that differs from the anticoagulant level in the donor/patient to whom the tubing set 81 is attached. In the present invention, MESEC may be empirically established for a broad class of donor/patients. The present invention may rely on published data and observation to empirically establish the MESEC above which extracorporeal blood does not clump and/or clot for the majority of donors/patients. The present invention may also establish the MESEC for a specific donor/patient as will be discussed in more detail below.

The present invention may calculate an anticoagulant infusion rate profile that will not exceed the generally applicable or specific MADEC but that will maximize the inlet flow rate at any time during the procedure and, therefore, the total amount of blood processed. The present invention also may calculate an inlet/AC ratio that will reduce the amount of anticoagulant added to the extracorporeal tubing set over time but will not allow the extracorporeal anticoagulant to fall below the generally applicable or specific MESEC. It has been observed that at a beginning of a procedure, an anticoagulant concentration greater than the MESEC is required to prevent clumping. The present invention incorporates this higher starting extracorporeal anticoagulant concentration in optimizing the inlet/AC ratio.

To predict the above described optimal infusion rate profile, the present invention first calculates the change in citrate concentration in the body of a donor/patient over time. The present invention uses a simplified one compartment version of a more general multi-compartment biodynamic model of citrate kinetics in the donor/patient to calculate the changing donor/patient citrate concentration. It will be apparent to those skilled in the art, that models comprising any number of compartments for describing the kinetics of a constituent, such as citrate, in the body of a donor/patient may be used with the present invention. It will also be apparent to those skilled in the art that where citrate is used as the anticoagulant, a model describing the kinetics of calcium in the body of the donor/patient may be used with the present invention.

Figure 2:
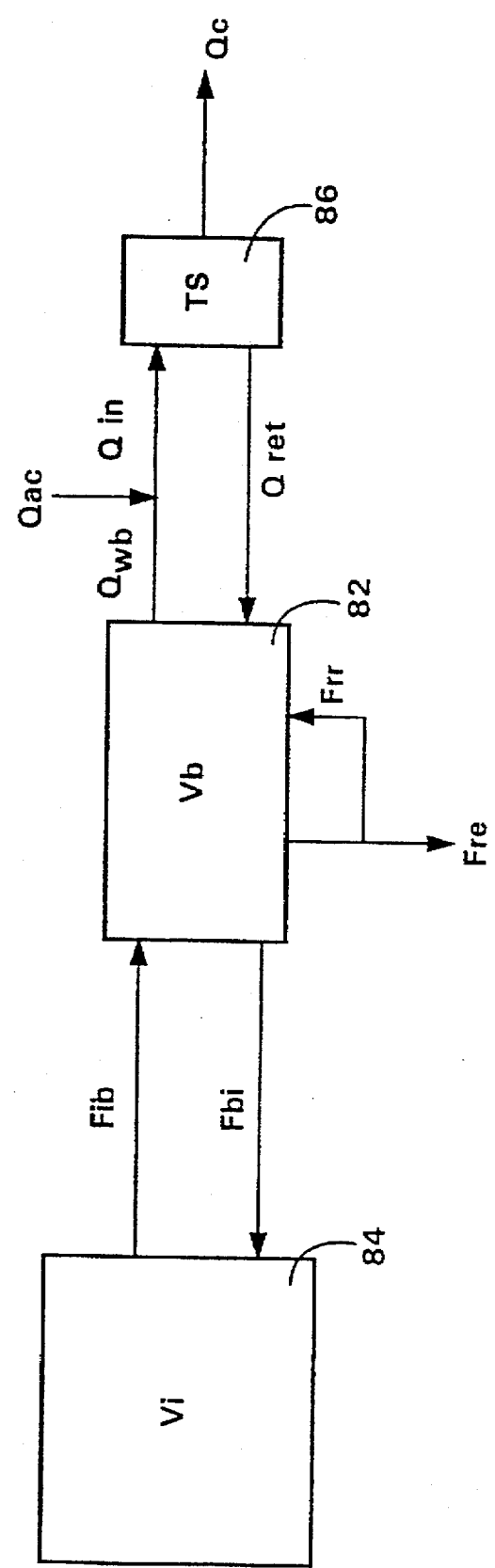
FIG. 2 is a simplified schematic drawing of a multi-compartment model of citrate accumulation in a donor/patient usable with the present invention.

FIG. 2 schematically illustrates the more general multi-compartment model of the present invention. The first compartment $V_b$ 82 conceptually correlates to a donor/patient's total blood volume ("TBV") and part of the donor/patient's interstitial fluid. The second compartment $V_i$ 84 conceptually correlates to the donor/patient's intracellular fluid and the remaining part of the donor/patient's interstitial fluid. The blood volume $V_{TS}$ in the tubing set 81 is represented by the box 86.

The whole blood flow from the donor/patient to the extracorporeal tubing set 81 is denoted by $Q_{wb}$. The anticoagulated blood flow in the inlet line 12 of the tubing set 81 is denoted by $Q_{in}$. The anticoagulant flow from the anticoagulant reservoir 14 to the inlet line 12 of the tubing set 81 is denoted by $Q_{ac}$. The collected blood component flow is denoted by $Q_c$. The return blood flow from the tubing set 81 to the donor/patient is denoted by $Q_{ret}$.

The citrate transfer rate from the first compartment 82, in the donor/patient, to the second compartment 84 is denoted by $F_{bi}$ while the citrate transfer rate from the second compartment 84 to the first compartment 82, in the donor/patient, is denoted by $F_{ib}$. The citrate transfer rate from the donor/patient due to renal clearance, metabolic breakdown and endogenous citrate production is denoted by $F_{re}$. The citrate transfer rate from renal reabsorption is denoted by $F_{rr}$.

The citrate kinetics illustrated in FIG. 2 are calculated over time to account for the effect of renal citrate clearance, renal citrate reabsorption, metabolic citrate clearance and endogenous citrate production on citrate accumulation in a donor/patient as described by the following equations. It should be understood that the following equations contain common terms. A term defined for one equation is defined in the same manner for the following equation. Therefore, each equation will only define new terms that were not previously defined in the preceding equations.

The following relationships completely define the donor/patient citrate model schmaticized in FIG. 2

$V_B = aV_{TB}$ $V_I = bV_{TB}$ $F_{BI} = K_{BI}V_BC_B$ $F_{IB} = K_{IB}V_IC_I$ $F_{RE} = K_{RE}V_BC_B$ $F_{RR} = K_{RR}V_{TB}$

Where $V_{TB}$=the donor/patient total blood volume in mls.

$C_B$=citrate concentration in $V_B$, in µmol per ml.

$C_I$=citrate concentration in $V_I$, in µmol per ml.

a, b, K=constants emprically determined by correlating the model to measured citrate concentrations in human subjects.

By correlating the above described model to three independent sets of published data, the values of the following constants were found to be:

$K_{BI}$=0.5 min$^{-1}$ $K_{IB}$=0.2 min$^{-1}$ $K_{RE}=0.14 \text{ min}^{-1}$ $K_{RR}=aK_{RE}C_{BO}=0.224C_{BO} \text{ } \mu\text{mol/ml/min}^{-1}$ Where $C_{BO}$=the initial conditions for $C_B$ when t=0

The inlet flow rate is defined by:

$$Q_{in}=\frac{IRV_{TB}P}{1000}$$

Where

I=anticoagulant infusion rate to the donor/patient in ml/min per liter of TBV.

R=$Q_{in}/Q_{AC}$=the inlet/AC ratio defined above.

P=ratio of anticoagulated blood flow in the inlet line 12 to anticoagulated blood flow in the outlet line 34 to the patient.

The purpose of the above model is to estimate $C_B$ as a function of time when I, R, P, and $C_{BO}$ are known. P is determined by the details of how a procedure is conducted for a particular donor/patient as described in the co-pending parent application Reg. No. 07/845,677 incorporated above by reference. In order to develop generalized equations for the optimum control of citrate infused to the donor/patient, for the purpose of maximizing the volume of blood processed during a given procedure time, the model is analyzed as follows.

For a constant R and I the model is used to develop an equation that estimates $C_B$ as a function of time. It will be apparent to one skilled in the art that analytically solving linear differential equations based on citrate balances around $V_B$ and $V_I$ in the conventional manner will estimate $C_B$ as a function of time.

The present invention uses these linear differential equations to derive a mathematical transfer function. The mathematical transfer function is used, in the conventional manner, to develop an explicit equation for I, as a function of time that will give any desired $C_B$, also as a function of time. This equation for I represents the optimum time profile for the anticoagulant infusion rate that will satisfy the desired $C_B$ profile, where it is desired that the donor/patient citrate concentration approach MADEC as rapidly as practical constraints on $Q_{IN}$ will allow and, thereby maximize the total volume of blood processed during the procedure. The invention adapts the explicit equation for I and adapts it for use in a controller 80. The present invention uses the $C_B$ estimated by the explicit equation for I described above to maximize the inlet/AC ratio R by accounting for unmetabolized citrate recirculated from the donor/patient to the extracorporeal tubing set 81. The present invention also accounts for the higher extracorporeal citrate concentration observed to be required at the beginning of a procedure.

It was found that a simplified single compartment version of this more general multi-compartment model could be used to adequately account for the above described physiological processes. The inventors found that the simplified single compartment model may calculate, substantially as accurately as the multi-compartment model, the change of citrate concentration in a donor/patient with time. The present invention, using a simplified single compartment model of the above described multi-compartment model, calculates an optimal anticoagulant infusion rate profile that will maximize the inlet flow rate. One way to maximize the inlet flow rate is to achieve the MADEC relatively fast and remain at the MADEC for the remainder of the procedure time. This increases the inlet flow rate at the beginning of a procedure, thereby, increasing the total amount of blood processed during the procedure.

As mentioned above, it should be understood that the following equations contain common terms. A term defined for one equation is defined in the same manner for the following equation. Therefore, each equation will only define new terms that were not previously defined in the preceding equations. In the following equations, the subscript B has been eliminated because it is superfluous in designated donor/patient citrate concentrations.

The following equations are defined to accommodate many procedure requirements, including arbitrary limitations imposed on the inlet flow rate $Q_{IN}$ at any time during a procedure. Thus $t_1$ is defined as any time during or at the start of the procedure that a new constraint is imposed $Q_{IN}$ for any reason, including adjustments to MADEC to accommodate donor/patient specificity.

The presently preferred embodiment of the present invention comprises defining the desired optimum profile for C to be that of a critically damped first order function given by:

$$C=C_0+(C_{CRIT}-C_0)[1-\exp(-\gamma\alpha t)]$$

Where $C_{CRIT}$=MADEC, $\mu$mol/ml $\gamma$=parameter that determines the rate at which C approaches $C_{CRIT}$ $\alpha$=decay constant for the single compartment model, =0.0348 min$^{-1}$ t=time, in minutes $C_0$=C at t=0, $\mu$mol/min The corresponding expression for the citrate infusion rate I is:

$$I/I_{CRIT}=1+(\gamma-1)\exp(-\gamma\alpha t)$$

The explicit equations resulting from using these two optimum relationships for C and I derived from all the preceding modelling considerations are as follows:

1. All inlet flow limitations $Q_{INMAX}$ are incorporated in the present invention by imposing a limit on I as follows:

$$I_{MAX}=1000Q_{INMAX}/RPV_{TB}$$

2. MADEC is expressed in terms of a corresponding critical value for I as $$I_{CRIT}=(C_{CRIT}-C_0)(1000\alpha a/C_{AC})$$

Where for the single compartment model a=6.44

$C_{AC}$=113 $\mu$mol/ml for the commonly used anticoagulant ACD.

$C_0$=is donor/patient specific and is may be approximated at 0.1 nmol/ml $C_{CRIT}$=is donor specific and may be approximated at 0.5 to 1.0 $\mu$mol/ml.

3. The optimum anticoagulant infusion profile beginning at some time, t, may be given as follows:

$$I=I_{CRIT}[1+(\gamma-1)\exp[-\gamma\alpha(t-t_1)]]$$

4. The limit on $\gamma$ imposed by the limit $I_{MAX}$ which is in turn determined by the limit $Q_{MAX}$ is:

$$\gamma=I_{MAX}/I_{CRIT}\geq 1$$

If $I_{MAX}/I_{CRIT}\leq 1$, then the optimized anticoagulant infusion profile will not allow more blood to be processed than a constant anticoagulant infusion rate.

5. The estimation of C beyond any time $t_1$ is given by:

$$C = C_0 + (C_1 - C_0) \exp[-\alpha(t-t_1)] + (C_{CRIT} - C_0)[1 - \exp[-\gamma\alpha(t-t_1)]]$$

This equation is used to calculate $C_1$ for each subsequent $t_1$.

Where controller 80 comprises a micro processor, the above equations may be repetitively reevaluated every few seconds; thus, if any conditions change, control of the system, including anticoagulant infusion rate control adapts accordingly.

The present invention may also vary the level of extracorporeal anticoagulant with time. The present invention may account for unmetabolized citrate recirculated from the donor/patient to the received blood in the inlet line 12 in determining the appropriate anticoagulant delivery rate to maintain the predetermined MESEC. If the procedure length and volume of blood processed is sufficiently large such that anticoagulant build up in the donor/patient becomes significant, the rate at which anticoagulant is added to the inlet blood from the anticoagulant reservoir 14 via the anticoagulant line 18 is varied with time to account for the unmetabolized citrate recirculated from the donor/patient into the inlet line 12.

Where the infusion rate of anticoagulated blood to the donor/patient is being varied to rapidly achieve and maintain the maximum citrate concentration tolerable in the donor/patient, the rate of anticoagulant addition to the inlet line 12 may be adjusted to achieve the appropriate ratio of inlet flow rate to anticoagulant flow rate R, as follows:

$$R = (C_{AC} - C)/(C_{TS} - C)$$

Where $C_{TS}$ = The target extracorporeal citrate concentration in the tubing set 81.

It has been observed that higher extracorporeal concentrations are needed during the beginning of a procedure than are required by MESEC. The extracorporeal anticoagulant concentration at a beginning of a procedure, therefore, should be higher than MESEC. It is preferable, therefore, that $C_{TS}$ be a function of time. $C_{TS}$ may be fully donor/patient dependent and may be expressed as MESEC multiplied by a profiling function. After the beginning of a procedure, MESEC determines the minimum extracorporeal anticoagulant concentration in the extracorporeal tubing set 81. The above described extracorporeal anticoagulant concentration increase at the beginning of a procedure may be calculated as follows:

$$R = (C_{AC} - C)/(C_{TS} - C)$$

Figure 3:
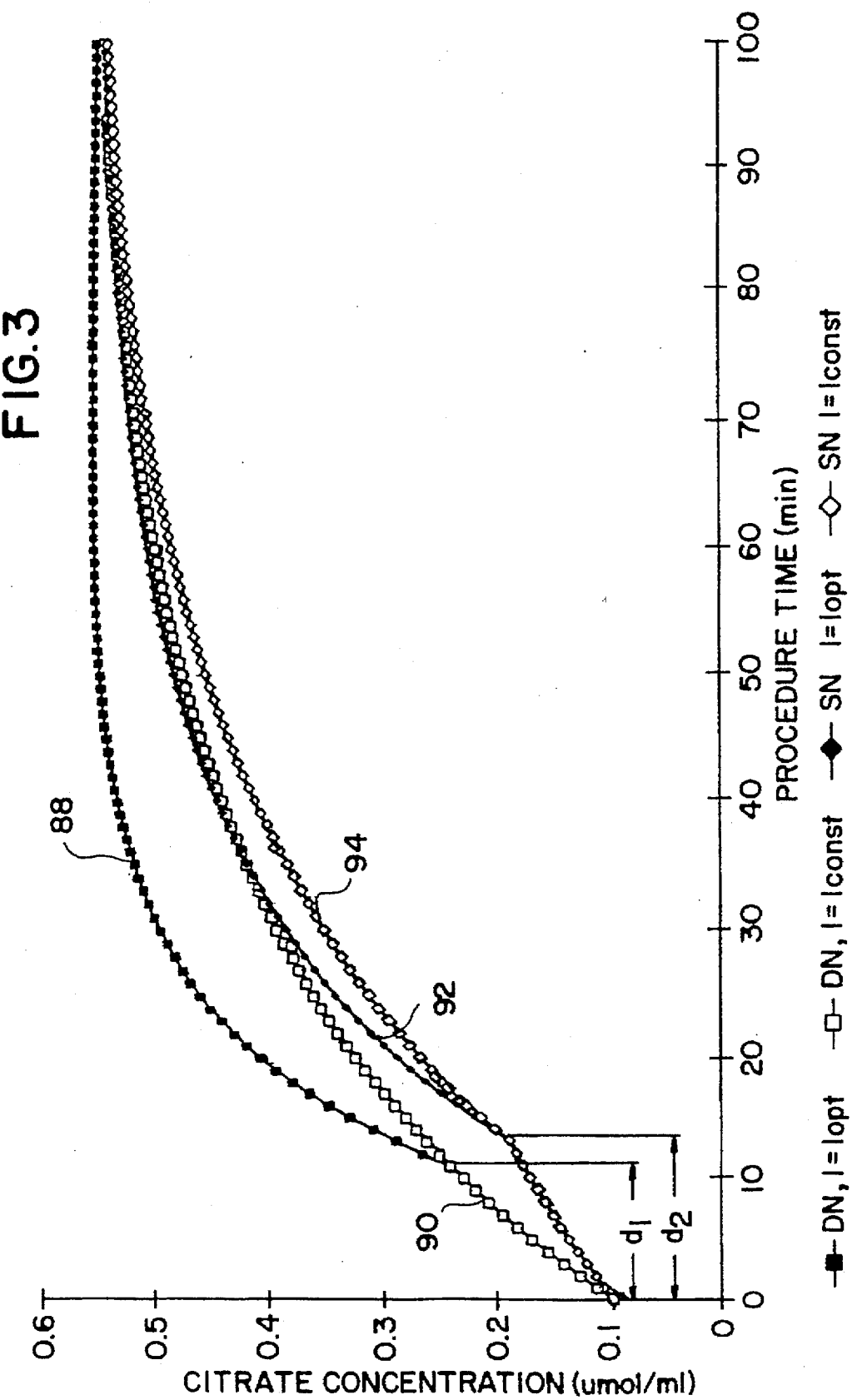
FIG. 3 is a graph comparing the accumulation of citrate in the body of a donor/patient where citrate is infused to the donor/patient at a constant infusion rate and at the optimized infusion rate profile of the present invention during both a single needle blood processing procedure.

FIG. 3 graphically illustrates that using the optimized anticoagulant infusion rate profile of the simplified single compartment model, results in a rapid donor patient citrate accumulation that then remains at or below the MADEC for the remainder of the procedure time. Citrate concentration in the donor/patient in µmol/ml is plotted along the vertical axis. Procedure time in minutes is plotted along the horizontal axis. The curve 88 represents the donor/patient citrate accumulation where anticoagulant is infused at the optimized infusion rate profile $I_{opt}$ of the present invention during a dual needle procedure ("DN"). The curve 90 represents the donor/patient citrate accumulation where anticoagulant is infused at a constant infusion rate $I_{const}$ during a dual needle procedure. The curve 92 represents the donor/patient citrate accumulation where anticoagulant is infused at the optimized infusion rate profile $I_{opt}$ of the present invention during a single needle procedure ("SNR"). The curve 94 represents the donor/patient citrate accumulation where anticoagulant is infused at a constant infusion rate $I_{const}$ during a single needle procedure.

The present invention may customize the MADEC and the MESEC for a specific donor/patient. If an optimized variable infusion rate is run for a given donor/patient and adverse side effects are observed, the MADEC may be adjusted downward by the medical care worker. Alternatively, the donor/patient citrate concentration at the onset side effects may be calculated, using the present invention. This calculated donor/patient citrate concentration may then be used as a basis to manually or automatically adjust the MADEC downwards. The present invention uses the new lower MADEC to calculate a new optimized variable infusion rate profile for the given donor/patient as described in the equations above. The new lower MADEC and new optimized variable infusion rate may be stored in the controller 80 of the present invention, for use with the given donor/patient in a future blood processing procedure. Similarly, if no adverse side effects are observed for the given donor/patient, the medical care worker may adjust the MADEC upward. The present invention uses the new higher MADEC to calculate a new optimized variable infusion rate as described in the equations above. Once again the new higher MADEC and optimized variable infusion rate may be stored in the controller 80 for future use with the given donor/patient.

Correspondingly, if a MESEC used with a given donor/patient results in clumping and/or clotting in the blood processor's tubing set, the medical care worker may adjust the MESEC upward. The present invention uses the new higher MESEC to calculate a new anticoagulant delivery rate to achieve an appropriate ratio of inlet flow rate to anticoagulant flow rate and, therefore, an appropriate anticoagulant concentration in the tubing set. This new MESEC and delivery rate may be stored in the controller 80 for future use with the given donor/patient.

As mentioned above, the invention can also be used with heparin, or any anticoagulant having a predictable decay rate, although some adjustment of variables in the model may be required.

The description herein contemplates numerical calculations of anticoagulant levels for the purpose of monitoring or adjusting (or both) the anticoagulant levels. It will be apparent that actual numerical calculations may not be necessary to utilize the invention. Instead, for example, the invention may be used to make relative adjustments to various flow rates depending on various other flow rates and parameters so that anticoagulant levels are optimally established even though they are never actually quantified. Such procedures are intended to be within the scope of the claims.

Although the present invention has been described with reference to preferred embodiments, numerous modifications and variations can be made and still the result will come within the scope of the invention. No limitation with respect to the specific embodiments disclosed herein is intended or should be inferred.

We claim:

1. A method for regulating the amount of anticoagulant infused to a donor, comprising the steps of:

removing the blood from the donor;

treating the blood in the extracorporeal blood treatment apparatus;

returning at least a fraction of the processed blood to the donor at a flow rate;

infusing an amount of anticoagulant in blood to the donor at an anticoagulant infusion rate;

predicting a maximum level of anticoagulant that may be present in the donor;

estimating the level of anticoagulant in the donor;

varying the amount of anticoagulant added to the blood at an anticoagulant infusion rate so that the estimated level of anticoagulant in the donor does not exceed the predicted maximum level of anticoagulant in the donor;

and varying the flow rate of the processed blood returned to the donor to maximize the flow rate while simultaneously preventing the estimated level of anticoagulant in the donor from exceeding the predicted maximum level of anticoagulant in the donor.

2. The method of claim 1 further comprising:

predicting a minimum level of anticoagulant that may be present in the blood in the extracorporeal blood treatment apparatus;

estimating the level of anticoagulant in the blood in the extracorporeal blood treatment apparatus; and varying the amount of anticoagulant added to the blood to always exceed the minimum level of anticoagulant; wherein the step of varying the flow rate of the blood further comprises:

varying the flow rate of the processed blood returned to the donor to maximize the blood flow rate while simultaneously causing the estimated level of anticoagulant in the blood in the extracorporeal blood treatment apparatus to always exceed the predicted minimum anticoagulant level in the extracorporeal blood treatment apparatus.

3. The method of claim 2 wherein the step of varying the flow rate of the blood further comprises:

increasing the flow rate of blood in the extracorporeal blood treatment apparatus so that the estimated level of anticoagulant in the donor approaches, but does not exceed, the predicted maximum anticoagulant level in the donor.

4. The method of claim 3 wherein the step of varying the flow rate of the blood further comprises:

decreasing the flow rate of the blood in the extracorporeal blood treatment apparatus if the amount of anticoagulant that should be added to the blood to cause the estimated level of anticoagulant in the blood in the extracorporeal blood treatment apparatus to exceed the predicted minimum level of anticoagulant in the extracorporeal blood treatment apparatus would result in the estimated level of anticoagulant in the donor exceeding the predicted maximum level of anticoagulant in the donor.

5. The method of claim 1 wherein the step of varying the flow rate of the blood further comprises:

increasing the flow rate of blood in the extracorporeal blood treatment apparatus so that the estimated level of anticoagulant in the donor approaches, but does not exceed, the predicted maximum anticoagulant level in the donor.

6. The method of claim 1 wherein the step of predicting a maximum level of anticoagulant that may be present in the donor predicts a donor specific level.

7. A method for regulating the amount of anticoagulant infused to a donor, comprising the steps of:

removing the blood from the donor;

treating the blood in the extracorporeal blood treatment apparatus;

returning at least a fraction of the processed blood to the donor at a flow rate;

infusing an amount of anticoagulant in blood to the donor at an anticoagulant infusion rate;

predicting a minimum level of anticoagulant that may be present in the blood in the extracorporeal blood treatment apparatus;

estimating the level of anticoagulant in the blood in the extracorporeal blood treatment apparatus;

varying the amount of anticoagulant added to the blood at an anticoagulant infusion rate so that the estimated level of anticoagulant in the extracorporeal blood treatment apparatus does always exceed the predicted minimum level of anticoagulant in the blood in the extracorporeal blood treatment apparatus;

and varying the flow rate of the processed blood returned to the donor to maximize the flow rate while simultaneously causing the estimated level of anticoagulant in the blood in the extracorporeal blood treatment apparatus to exceed the predicted minimum level of anticoagulant in the extracorporeal blood treatment apparatus.

8. The method of claim 7 wherein the step of predicting a minimum level of anticoagulant that may be present in the blood in the extracorporeal blood treatment apparatus predicts a level that varies with time.

9. The method of claim 7 wherein the step of predicting a minimum level of anticoagulant that may be present in the blood in the extracorporeal blood treatment apparatus predicts a donor specific level.

10. An extracorporeal blood treatment apparatus for treating blood from a donor, comprising:

means for removing the blood from the donor; means for treating the blood;

means for returning at least a fraction of the processed blood to the donor at a flow rate;

means for predicting a maximum level of anticoagulant that may be present in the donor;

means for estimating the level of anticoagulant in the donor;

means for varying the amount of anticoagulant added so that the estimated level of anticoagulant in the donor does not exceed the predicted maximum level of anticoagulant in the donor;

and means for varying the flow rate of the processed blood returned to the donor to maximize the flow rate while simultaneously preventing the estimated level of anticoagulant in the donor from exceeding the predicted maximum level of anticoagulant in the donor.

11. The apparatus of claim 10 further comprising:

means for predicting a minimum level of anticoagulant that may be present in the blood in the extracorporeal blood treatment apparatus;

means for estimating the level of anticoagulant in the blood in the extracorporeal blood treatment apparatus; and means for varying the amount of anticoagulant added to the blood to always exceed the minimum level of anticoagulant; wherein the means for varying the flow rate of the blood further comprises:

means for varying the flow rate of the processed blood returned to the donor to maximize the blood flow rate while simultaneously causing the estimated level of anticoagulant in the blood in the extracorporeal blood treatment apparatus to always exceed the predicted minimum anticoagulant level in the extracorporeal blood treatment apparatus.

12. The apparatus of claim 11 wherein the means for varying the flow rate of the blood further comprises:

means for increasing the flow rate of blood in the extracorporeal blood treatment apparatus so that the estimated level of anticoagulant in the donor approaches, but does not exceed, the predicted maximum anticoagulant level in the donor.

13. The apparatus of claim 12 wherein the means for varying the flow rate of the blood further comprises:

means for decreasing the flow rate of the blood in the extracorporeal blood treatment apparatus if the amount of anticoagulant that should be added to the blood to cause the estimated level of anticoagulant in the blood in the extracorporeal blood treatment apparatus to exceed the predicted minimum level of anticoagulant in the extracorporeal blood treatment apparatus would result in the estimated level of anticoagulant in the donor exceeding the predicted maximum level of anticoagulant in the donor.

14. The apparatus of claim 10 wherein the means for varying the flow rate of the blood further comprises:

means for increasing the flow rate of blood in the extracorporeal blood treatment apparatus so that the estimated level of anticoagulant in the donor approaches, but does not exceed, the predicted maximum anticoagulant level in the donor.

15. An apparatus for treating blood from a donor in an extracorporeal blood treatment apparatus, comprising:

means for removing the blood from the donor;

means for treating the blood in the extracorporeal blood treatment apparatus;

means for returning at least a fraction of the processed blood to the donor at a flow rate;

means for predicting a minimum level of anticoagulant that may be present in the blood in the extracorporeal blood treatment apparatus;

means for estimating the level of anticoagulant in the blood in the extracorporeal blood treatment apparatus;

means for varying the amount of anticoagulant added to the blood so that the estimate level of anticoagulant in the extracorporeal blood treatment apparatus always exceeds the predicted minimum level of anticoagulant in the blood in the extracorporeal blood treatment apparatus;

and means for varying the flow rate of the processed blood returned to the donor to maximize the flow rate while simultaneously causing the estimated level of anticoagulant in the blood in the extracorporeal blood treatment apparatus to exceed the predicted minimum level of anticoagulant in the extracorporeal blood treatment apparatus.

* * * * *